(12) United States Patent
Kääriäinen et al.

(10) Patent No.: US 10,337,981 B2
(45) Date of Patent: Jul. 2, 2019

(54) LOW VOLUME MULTIPASS CELL

(71) Applicant: TEKNOLOGIAN TUTKIMUSKESKUS VTT OY, Espoo (FI)

(72) Inventors: Teemu Kääriäinen, Espoo (FI); Albert Manninen, Espoo (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 0 days.

(21) Appl. No.: 15/775,415

(22) PCT Filed: Nov. 3, 2016

(86) PCT No.: PCT/FI2016/050774
§ 371 (c)(1),
(2) Date: May 11, 2018

(87) PCT Pub. No.: WO2017/081363
PCT Pub. Date: May 18, 2017

(65) Prior Publication Data
US 2018/0372616 A1    Dec. 27, 2018

(30) Foreign Application Priority Data
Nov. 11, 2015   (FI) ...................... 20155833

(51) Int. Cl.
*G01N 21/25* (2006.01)
*G01N 21/03* (2006.01)
(Continued)

(52) U.S. Cl.
CPC ....... *G01N 21/031* (2013.01); *G01N 21/1702* (2013.01); *G01N 21/39* (2013.01);
(Continued)

(58) Field of Classification Search
CPC ........ G01N 21/03; G01N 21/17; G01N 21/31; G01N 29/24; G01N 21/00; G01N 21/39;
(Continued)

(56) References Cited

U.S. PATENT DOCUMENTS 4,189,646 A * 2/1980 Vanderleeden ........ B01D 59/34
204/157.22
5,094,533 A   3/1992 Sawada et al.
(Continued)

FOREIGN PATENT DOCUMENTS

CN   104122223 A   10/2014
DE   10216047 A1  10/2003
(Continued)

OTHER PUBLICATIONS

Rollason, A.J. et al. 'Multipass optical cavity for inverse Compton interactions', Nuclear Instruments and Methods in Physics Research A, 2004, vol. 526, No. 3, pp. 560-571.
(Continued)

*Primary Examiner* — Abdullahi Nur
(74) *Attorney, Agent, or Firm* — Robert P. Michal, Esq.; Carter, DeLuca & Farrell LLP

(57) ABSTRACT

A multipass cell, includes a body; a cavity formed within the body; a first spherical or toroidal mirror at a first end of the cavity; and a second spherical, toroidal or cylindrical mirror at the opposite end of the cavity. The first mirror and the second mirror are configured to reflect a beam entering the cavity next to an outer edge of the first or the second mirror a predetermined number of times so that the beam propagates substantially in a single plane between the first and the second mirror. Also an optical detection system includes the multipass cell; an optical source configured to direct a beam into the cavity; and a detector element configured to receive
(Continued)

the beam exiting the cavity or configured to receive the acoustic signal generated by light absorption in the cavity.

10 Claims, 4 Drawing Sheets

(51) Int. Cl.
*G02B 17/00* (2006.01)
*G01N 21/17* (2006.01)
*G01N 21/39* (2006.01)
*G01N 29/02* (2006.01)
*G01N 29/24* (2006.01)
*G01N 21/3504* (2014.01)

(52) U.S. Cl.
CPC ......... *G01N 29/02* (2013.01); *G01N 29/2425* (2013.01); *G02B 17/00* (2013.01); *G02B 17/004* (2013.01); *G01N 21/3504* (2013.01); *G01N 2021/1704* (2013.01)

(58) Field of Classification Search
CPC .... G01N 33/49; G01J 3/42; G01J 3/02; G01J 3/14; G01J 3/18; H01S 5/40
See application file for complete search history.

(56) References Cited

U.S. PATENT DOCUMENTS

| | | | |
|---|---|---|---|
| 5,121,988 A * | 6/1992 | Blesener | G01N 15/1434 250/574 |
| 5,993,549 A | 11/1999 | Kindler et al. | |
| 6,067,840 A | 5/2000 | Chelvayohan et al. | |
| 2001/0051118 A1 | 12/2001 | Mosso et al. | |
| 2002/0057432 A1 | 5/2002 | Ortyn et al. | |
| 2010/0079760 A1 | 4/2010 | Bernacki | |
| 2010/0107733 A1 | 5/2010 | Miklos et al. | |
| 2017/0356842 A1 * | 12/2017 | Rao | G01N 21/1702 |

FOREIGN PATENT DOCUMENTS

| | | |
|---|---|---|
| EP | 1509759 A1 | 3/2005 |
| FR | 2767195 A1 | 2/1999 |
| GB | 1168717 A | 10/1969 |
| JP | H0843305 A | 2/1996 |
| JP | 2003050202 A | 2/2003 |

OTHER PUBLICATIONS

International Search Report issued by the Finnish Patent and Registration Office acting as the International Searching Authority in relation to International Patent Application No. PCT/FI2016/050774 dated Feb. 3, 2017 (6 pages).

Written Opinion of the International Searching Authority issued by the Finnish Patent and Registration Office acting as the International Searching Authority in relation to International Patent Application No. PCT/FI2016/050774 dated Feb. 3, 2017 (10 pages).

Finnish Search Report issued by the Finnish Patent and Registration Office in relation to Finnish Application No. 20155833 dated Apr. 21, 2016 (3 pages).

Extended European Search Report issued by the European Patent Office in relation to European Application No. 16863728.8 dated Mar. 19, 2019 (25 pages).

* cited by examiner

US 10,337,981 B2

LOW VOLUME MULTIPASS CELL

CROSS-REFERENCE TO RELATED APPLICATIONS

This application is a national phase entry under 35 U.S.C. 371 of PCT International Application No. PCT/FI2016/050774 filed Nov. 3, 2016, which claims priority to Finnish Patent Application No. 20155833, filed Nov. 11, 2015 the disclosure of each of these applications is expressly incorporated herein by reference in their entirety.

TECHNICAL FIELD

The present application generally relates to optical detection. In particular, but not exclusively, the present application relates to a low volume optical multipass cell for use in optical detection, for example in laser spectroscopy.

BACKGROUND

This section illustrates useful background information without admission of any technique described herein being representative of the state of the art.

Sensitivity of optical detection, for example in laser spectroscopy, can be improved by increasing the optical pathlength within the sample being analyzed. Such an increase of optical pathlength is conveniently obtained using a multipass cell. Conventional multipass cells, e.g. Herriott cells, are well known. Such conventional multipass cells require a large volume and are accordingly unsuitable for applications with limited space and/or low available sample volume.

Previously a multipass cell with circular beam pattern has been disclosed in patent publication U.S. Pat. No. 7,876,443 B. Such a multipass cell can be fitted into a relatively low volume. However, such a cell is difficult to produce even with modest optical surface quality and accordingly such a cell is expensive.

A circular multipass cell constructed from separate sections has also been previously presented in a journal article *"Versatile multipass cell for laser spectroscopic trace gas analysis"* by Manninen et. al. in Applied Physics B (2012) 109, p. 461-466. However, such a cell, while more cost-effective, requires very tasking alignment of the separate mirrors and problems arise with diffraction on the mirror edges.

Furthermore, concave mirrors opposite to one another have been disclosed in patent publication U.S. Pat. No. 5,786,893 for use in focusing and pumping laser light from several sources into a sample region of a Raman spectrometer.

It is the aim of the current invention to provide a multipass cell that mitigates for example the above problems of the state of the art and/or provides a high optical path to sample volume ratio.

SUMMARY

Various aspects of examples of the invention are set out in the claims.

According to a first example aspect of the present invention, there is provided a multipass cell, comprising
a body;
a cavity formed within the body;
a first spherical, toroidal or cylindrical mirror at a first end of the cavity; and
a second spherical, toroidal or cylindrical mirror at the opposite end of the cavity; wherein
the first mirror and the second mirror are configured to reflect a beam entering the cavity next to an outer edge of the first or the second mirror a predetermined number of times so that the beam propagates substantially in a single plane between the first and the second mirror.

The first mirror and the second mirror may be configured in such a way that prior to the first reflection from the first or second mirror and after the last reflection from the first or second mirror the beam propagates substantially in the same single plane.

The multipass cell may further comprise at least a first channel configured to allow a beam to enter the cavity.

The multipass cell may further comprise at least a second channel configured to allow a beam to exit the cavity.

The multipass cell may further comprise means for introducing a sample in to the cavity.

The means for introducing a sample into the cavity may comprise a fluid inlet channel and a fluid outlet.

The multipass cell may further comprise a cover configured to cover the cavity.

The means for introducing a sample into the cavity may comprise perforations and/or porous material in the cover.

According to a second example aspect of the present invention, there is provided an optical detection system, comprising:
the multipass cell of the first aspect of the invention;
an optical source configured to direct a beam into the cavity; and
a detector element configured to receive the beam exiting the cavity or configured to receive the acoustic signal generated by light absorption in the cavity.

The optical source may comprise a tunable laser source configured to direct a laser beam of adjustable frequency or modulated intensity into the cavity.

The optical detection system may comprise a laser absorption spectrometer or a photoacoustic detector.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

The present invention and its potential advantages are understood by referring to FIGS. 1 through 7 of the drawings. In this document, like reference signs denote like parts or steps.

Figure 1A:
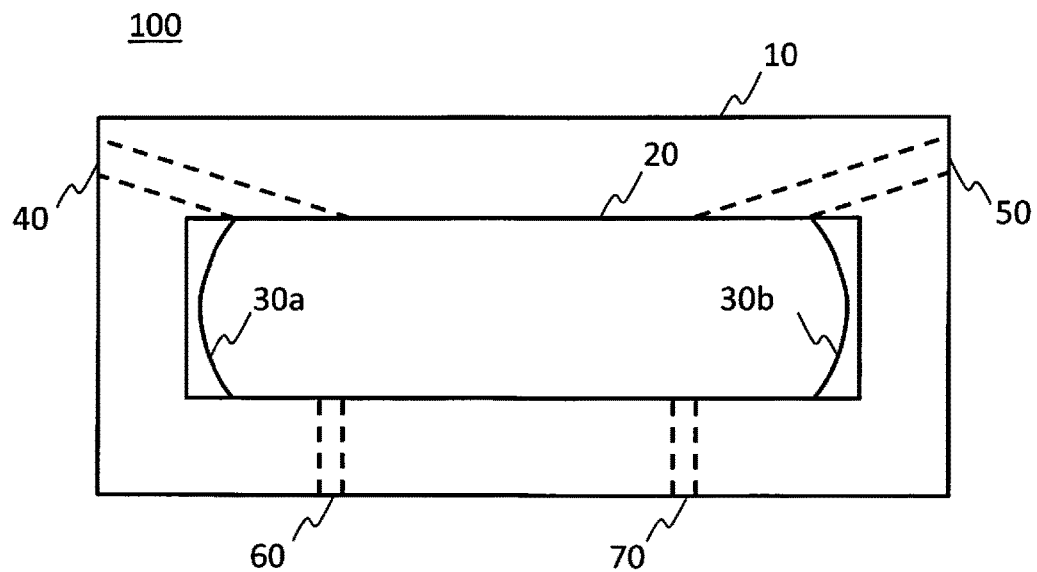
FIG. 1a shows a schematic top view of a multipass cell according to an embodiment of the invention.
Figure 1B:
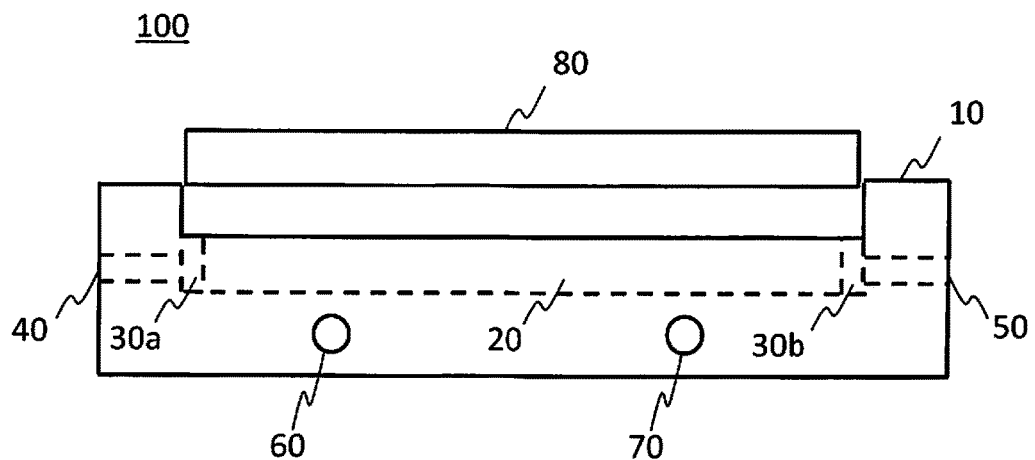
FIG. 1b shows a schematic side view of a multipass cell according to an embodiment of the invention.

FIGS. 1a and 1b show a schematic top and side view, respectively, of a multipass cell 100 according to an embodiment of the invention. The multipass cell 100 comprises a body 10. The body 10 is made of a suitable material, in an embodiment material such as plastic, glass, metal or composite materials or a composition comprising several materials. A cavity 20 is formed in the body 10 of the multipass cell 100. In an embodiment the cavity 20 has a rectangular form. In a further embodiment, the cavity has a form different from a rectangle, for example a cross section of the cavity 20 is in an embodiment circular. In a further embodiment, the cavity is thinner in the middle than at the ends thereof in order to minimize the volume thereof.

The multipass cell 100 further comprises a first mirror 30a and a second mirror 30b at opposite ends of the cavity 20, i.e. the first mirror 30a at a first end and the second mirror 30b at the other, opposite, end. The first and second mirrors 30a, 30b comprise concave spherical, toroidal, or cylindrical mirrors. In an embodiment, the mirrors 30a, 30b are positioned parallel to each other and perpendicular to the centerline of the cavity 20. In a further embodiment, the first and/or the second mirror is tilted with respect to the other mirror and/or with respect to a cross-sectional axis of the cavity 20. The mirrors 30a, 30b in an embodiment comprise materials such as dielectric material, aluminium and copper and are in an embodiment coated, e.g. with gold, silver or with a coating applied by thin film technology, to improve reflectivity. The mirrors 30a, 30b are easy to manufacture with high optical quality and cost-effectively.

The multipass cell 100 further comprises a first channel 40 and a second channel 50 configured to allow electromagnetic radiation, in an embodiment UV, visible or infrared light such as a laser beam, to enter and exit the cavity 20. In an embodiment, the first 40 and second 50 channel are positioned on the same side of the cavity 20 as shown in FIG. 1a. In a further embodiment, the first 40 and second 50 channel are positioned on opposite corners of the cavity 20. In a still further embodiment, the first 40 and second 50 channel are positioned at the same end of the cavity 20 on opposite sides thereof. In a yet further embodiment, the multipass cell 100 comprises only a single channel configured to allow light to enter and exit the cavity 20. In a yet further embodiment, the multipass cell 100 comprises a channel on each corner of the cavity. The first channel 40 is positioned in such a way that the light enters the cavity next to the outer edge of the first 30a or second 30b mirror, i.e. a beam entering the cavity passes close to the edge of the first 30a or second 30b mirror. The exact distance of the beam entering the cavity 20 from the edge of the mirror 30a, 30b depends on the angle in which the beam is to enter the cavity 20 and on the desired position at which the beam hits the opposite mirror 30a, 30b.

The multipass cell 100 further comprises means for introducing a sample into the cavity 20. In an example embodiment, the means comprise a fluid inlet 60 and a fluid outlet 70 configured to convey a fluid sample into and out of the cavity 20. In a further embodiment, the multipass cell 100 comprises a cover, or a lid, 80 configured to cover the cavity 20 and in an embodiment to seal the cavity 20 in fluid tight manner. In a further example embodiment, the cover 80 is porous and/or perforated in order to allow fluid, for example gas, to enter and exit the cavity 20.

The first 30a and second 30b mirror and the first channel 40 are aligned in such a way that a beam, such as a beam of infrared laser, entering the cavity through the first channel 40 next to the outer edge of the first mirror 30a hits the second mirror 30b next to the opposite edge thereof. In an embodiment, the first 30a and the second 30b mirror are positioned at a distance corresponding to twice the radius of curvature of the first 30a and the second 30b mirror in such way that the beam is focused between the first 30a and the second 30b mirror. The first 30 and second 30b mirror are configured to reflect the beam entering the cavity next to an outer edge of the first 30a or the second 30b mirror a predetermined number of times so that the beam propagates substantially in a single plane between the first and the second mirror 30a, 30b and forms a substantially linear reflection spot pattern on the first 30a and the second 30b mirror. In an embodiment, the beam propagates in the cavity 20 prior to the first reflection from the first or second mirror 30a, 30b and after the last reflection from the first or second mirror 30a, 30b substantially in the same single plane. After several reflections, the beam exits the cavity next to the outer edge of the first 30a or the second 30b mirror depending on the position of the second channel 50. The number of reflections and the exit position depends on the alignment of the mirrors and the optical parameters thereof. In the following the propagation of a beam in the multipass cell 100 is explained further with reference to FIGS. 2 to 6.

Figure 2:
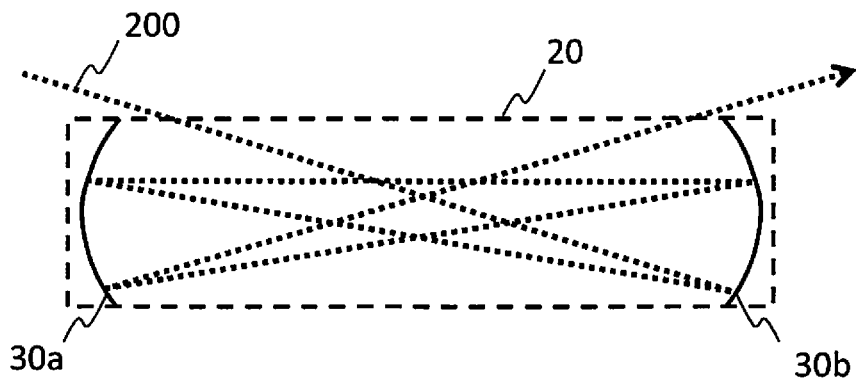
FIG. 2 shows a schematic principle view of a multipass cell according to an embodiment of the invention.

FIG. 2 shows a schematic principle view of a multipass cell according to an embodiment of the invention. A beam 200 enters the cavity 20 just outside the edge of the first mirror 30a and hits the opposite edge of the second mirror 30b. The first 30 and second 30b mirror are configured to reflect the beam entering the cavity next to an outer edge of the first 30a or the second 30b mirror a predetermined number of times so that the beam 200 propagates substantially in a single plane between the first and the second mirror 30a, 30b and forms a substantially linear reflection spot pattern on the first 30a and the second 30b mirror. After several reflections, the beam 200 exits the cavity just outside the edge of the second mirror 30b on the same side of the cavity from which it entered.

Figure 3:
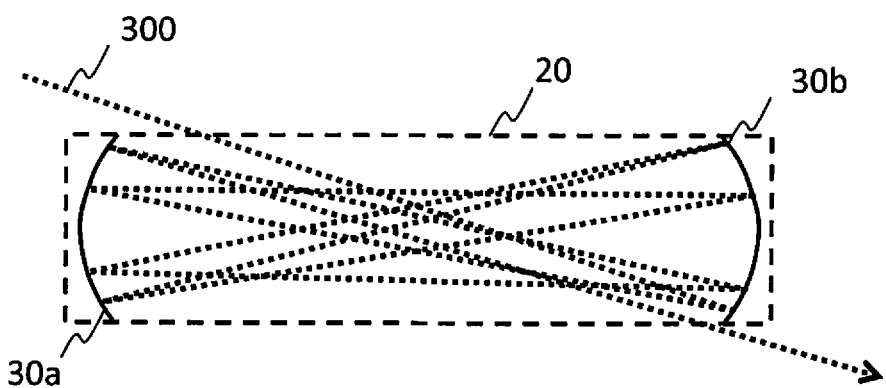
FIG. 3 shows a further schematic principle view of a multipass cell according to an embodiment of the invention.

FIG. 3 shows a further schematic principle view of a multipass cell according to an embodiment of the invention. A beam 300 enters the cavity 20 just outside the edge of the first mirror 30a and hits the opposite edge of the second mirror 30b. The first 30 and second 30b mirror are configured to reflect the beam entering the cavity next to an outer edge of the first 30a or the second 30b mirror a predetermined number of times so that the beam 300 propagates substantially in a single plane between the first and the second mirror 30a, 30b and forms a substantially linear reflection spot pattern on the first 30a and the second 30b mirror. After several reflections, the beam 300 exits the cavity just outside the edge of the second mirror 30b on the opposite side of the cavity from which it entered.

Figure 4:
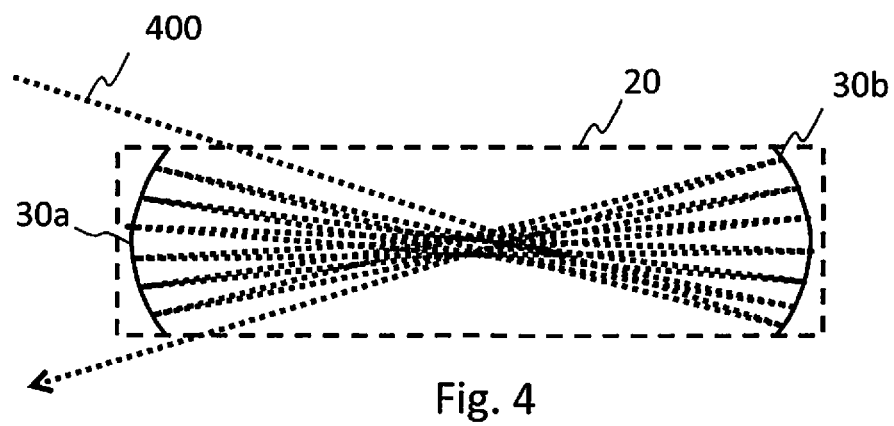
FIG. 4 shows a further schematic principle view of a multipass cell according to an embodiment of the invention.

FIG. 4 shows a further schematic principle view of a multipass cell according to an embodiment of the invention. A beam 400 enters the cavity 20 just outside the edge of the first mirror 30a and hits the opposite edge of the second mirror 30b. The first 30 and second 30b mirror are configured to reflect the beam entering the cavity next to an outer edge of the first 30a or the second 30b mirror a predetermined number of times so that the beam 400 propagates substantially in a single plane between the first and the second mirror 30a, 30b and forms a substantially linear reflection spot pattern on the first 30a and the second 30b mirror. After several reflections, the beam 400 exits the cavity just outside the edge of the first mirror 30a on the opposite side of the cavity from which it entered.

Figure 5:
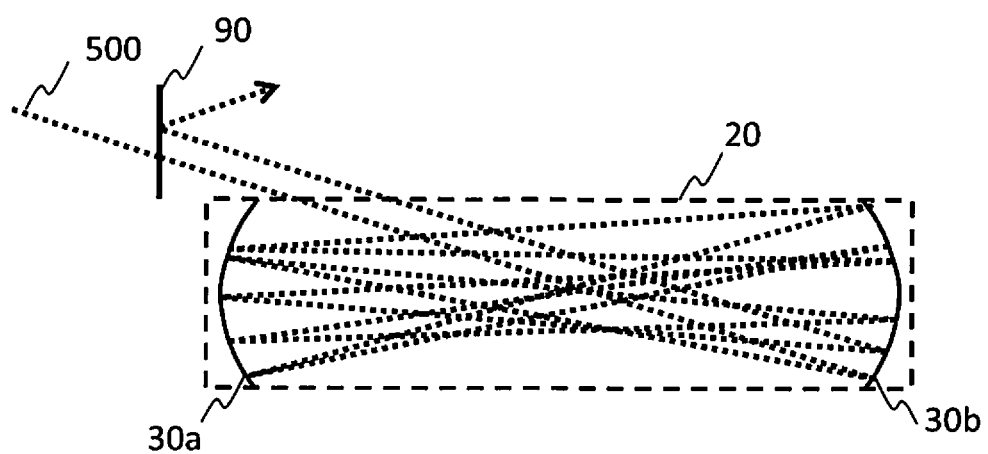
FIG. 5 shows a further schematic principle view of a multipass cell according to an embodiment of the invention.

FIG. 5 shows a further schematic principle view of a multipass cell according to an embodiment of the invention. A beam 500 enters the cavity 20 just outside the edge of the first mirror 30a and hits the opposite edge of the second mirror 30b. The first 30 and second 30b mirror are configured to reflect the beam entering the cavity next to an outer edge of the first 30a or the second 30b mirror a predetermined number of times so that the beam 500 propagates substantially in a single plane between the first and the second mirror 30a, 30b and forms a substantially linear reflection spot pattern on the first 30a and the second 30b mirror. After several reflections, the beam 500 exits the cavity just outside the edge of the first mirror 30a on the same side of the cavity from which it entered. In an embodiment, the multipass cell 100 further comprises an optical element 90, such as a beamsplitter or a mirror, configured to reflect the light exiting the cavity 20 into a desired direction, for example away from the source of the beam 500 towards e.g. a detector element.

Figure 6:
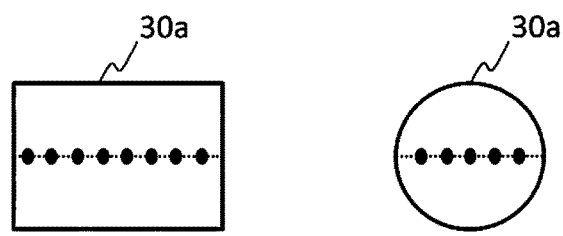
FIG. 6 shows a schematic principle view of reflection spot patterns of a multipass cell according to an embodiment of the invention.

FIG. 6 shows a schematic principle view of reflection spot patterns of a multipass cell according to an embodiment of the invention. FIG. 6 shows only the first mirror 30 with two example forms thereof. The first 30 and second 30b mirror are configured to reflect the beam entering the cavity next to an outer edge of the first 30a or the second 30b mirror a predetermined number of times so that the beam propagates substantially in a single plane between the first and the second mirror 30a, 30b and forms a substantially linear reflection spot pattern on the first 30a and the second 30b mirror. Accordingly, the cavity 20 need not have a large height, i.e. volume, as the beam propagation does not require height in comparison with traditional multipass cells with an elliptic reflection spot pattern.

The number of reflections, and accordingly the optical pathlength attained, depends on the alignment of the mirrors 30a, 30b, the optical parameters of the mirrors 30a, 30b and the size of the cavity 20, as well as the entry angle of the beam 200. The number of reflections is accordingly chosen in accordance with the use of the multipass cell, i.e. the needed pathlength and the size of the cavity required. The minimum size of the cavity is somewhat limited by diffraction depending on the wavelength of the used radiation. An example minimum length of the cavity 20 is for example with mid-infrared radiation, i.e. wavelengths of about 3 to 5 µm, approximately from 10 µm to 100 µm. In an embodiment, the minimum height of the cavity is in the region of a few millimeters, for example 2 millimeters.

Figure 7:
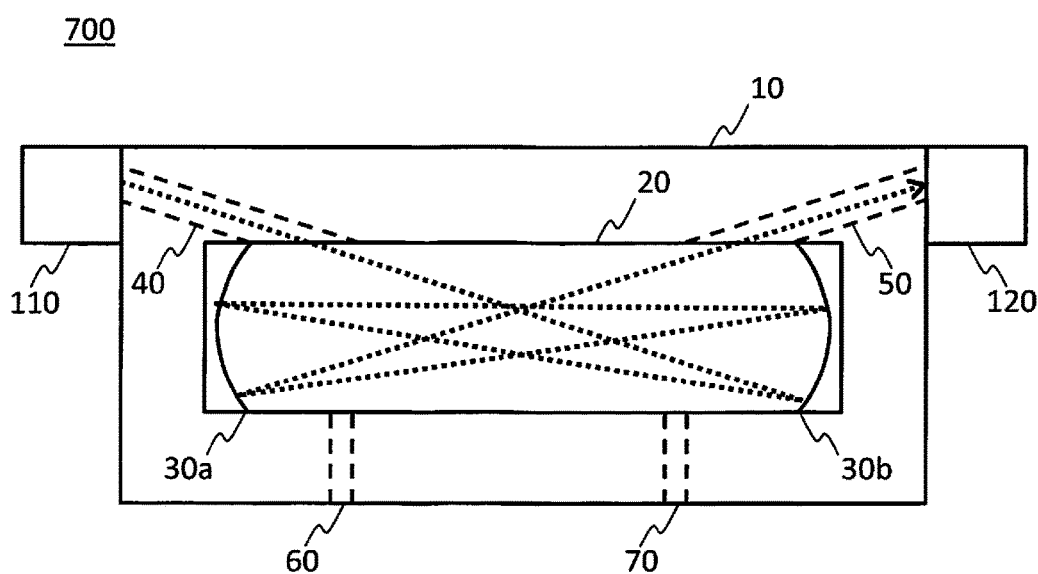
FIG. 7 shows a schematic top view of an optical detection system according to an embodiment of the invention.

FIG. 7 shows a schematic top view of an optical detection system 700 according to an embodiment of the invention. In embodiment, the optical detection system is a laser spectrometer. In a further embodiment the optical detection system is a laser absorption spectrometer. In a still further embodiment, the optical detection system is a photoacoustic detector. The optical detection system 700 comprises a multipass cell 100 as hereinbefore described with reference to FIGS. 1a to 6. The optical detection system 700 further comprises a source 110, for example a laser source configured to direct a beam into the cavity 20. In an embodiment, the source 110 comprises a tunable laser source, for example a mid-range infrared source, configured to direct a laser beam with adjustable frequency into the cavity 20 via the channel 40. The laser source 110 is of a conventional type. In a further embodiment, the laser source comprises a light emitting diode instead of a laser source. In a still further embodiment, the optical detection system 700 comprises several sources configured to direct a beam into the cavity 20 via a single or several channels.

The optical detection system 700 further comprises a detector element 120 configured to receive the beam exiting the cavity 20 via the channel 50. The detector element 120 comprises in an embodiment photodetectors and reference photodetectors and an interferometer. The detector element 120 is of a conventional type. In a further embodiment, the source 110 is configured to function as the detector element as well using e.g. so called self-mixing technique. In a still further embodiment the detector element 120 comprises an acoustic detection arrangement for photoacoustic detection configured to receive the acoustic signal generated by light absorption in the cavity 20.

The optical detection system 700 with the multipass cell 100 according to the invention is used for example in absorption laser spectrometry for detecting isotopes in a gas. In such an application a small sample volume with large pathlength is required with small interferences. In a further example, the optical detection system 700 with the multipass cell 100 is used in detecting temporal variations of concentration in which large sample exchange rates possible due to the small volume of the cavity 20 are required. In a still further example, the absorption laser spectrometry 700 with the multipass cell 100 is used in studying sample containing only a few molecules of the substance to be detected, which detection is possible due to the small amount of sample required as the volume of the cavity 20 is small and the pathlength large. In a yet further example, the multipass cell 100 according to the invention is scaled in such a way that it is installed in a handheld device, such as a mobile communications device, which is possible due to the small volume of the cavity 20.

Without in any way limiting the scope, interpretation, or application of the claims appearing below, a technical effect of one or more of the example embodiments disclosed herein is a simple alignment of the mirrors, i.e. the adjustment of distance and tilt thereof is straightforward. Another technical effect of one or more of the example embodiments disclosed herein is a robust multipass cell not sensitive to slight misalignment. Another technical effect of one or more of the example embodiments disclosed herein is a cost-effective multipass cell with components being easy to manufacture with high optical quality. A still further technical effect of one or more of the example embodiments disclosed herein is scalability, i.e. the provision of large pathlength in small volume.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications which may be made without departing from the scope of the present invention as defined in the appended claims.

The invention claimed is:

1. A multipass cell, comprising:
   a body;
   a cavity formed within the body;
   at least a first channel configured to allow a beam to enter the cavity;
   a first concave spherical, toroidal or cylindrical mirror at a first end of the cavity; and
   a second concave spherical, toroidal or cylindrical mirror at the opposite end of the cavity; wherein
   the first mirror and the second mirror are configured to reflect a beam entering the cavity just outside an outer edge of the first or the second mirror a predetermined number of times so that the beam propagates substantially in a single plane between the first and the second mirror, and wherein the first mirror and the second mirror are positioned in such a way that the beam is focused between the first and the second mirror.

2. The multipass cell of claim 1, wherein the first mirror and the second mirror are configured in such a way that prior to the first reflection from the first or second mirror and after the last reflection from the first or second mirror the beam propagates substantially in the same single plane.

3. The multipass cell of claim 1, further comprising at least a second channel configured to allow a beam to exit the cavity.

4. The multipass cell of claim 1, further comprising means for introducing a sample into the cavity.

5. The multipass cell of claim 4, wherein the means for introducing a sample into the cavity comprise a fluid inlet channel and a fluid outlet.

6. The multipass cell of claim 1, further comprising a cover configured to cover the cavity.

7. The multipass cell of claim 6, wherein the means for introducing a sample into the cavity comprise perforations and/or porous material in the cover.

8. An optical detection system, comprising:
   the multipass cell of claim 1;
   an optical source configured to direct a beam into the cavity; and
   a detector element configured to receive the beam exiting the cavity or configured to receive the acoustic signal generated by light absorption in the cavity.

9. The optical detection system of claim 8, wherein the optical source comprises a tunable laser source configured to direct a laser beam of adjustable frequency or modulated intensity into the cavity.

10. The optical detection system of claim 8, wherein the optical detection system comprises a laser absorption spectrometer or a photoacoustic detector.

* * * * *